United States Patent [19]

McCormick

[11] Patent Number: 4,557,903

[45] Date of Patent: Dec. 10, 1985

[54] APPARATUS FOR PREPARING AND EMBEDDING TISSUE SAMPLES FOR HISTOLOGICAL EXAMINATION

[75] Inventor: James B. McCormick, Chicago, Ill.

[73] Assignee: Pelam, Inc., Chicago, Ill.

[21] Appl. No.: 533,148

[22] Filed: Sep. 16, 1983

[51] Int. Cl.⁴ ............................................. B01L 11/00
[52] U.S. Cl. ................................... 422/101; 128/760; 206/439; 249/83; 422/102; 425/84; 425/117
[58] Field of Search ................. 249/83, 160, 170, 127, 249/92; 425/117, 84, 446, 423; 264/254, 275, 279, 292, 320, 322, DIG. 48, DIG. 70, 252; 350/536; 434/297; 206/484.1, 439; 83/915.5; 210/224, 228, 231; 422/101, 99, 102

[56] References Cited

U.S. PATENT DOCUMENTS

| | | | |
|---|---|---|---|
| 1,065,040 | 6/1913 | Garner | 434/297 |
| 2,996,762 | 8/1961 | McCormick | 264/238 |
| 3,319,289 | 5/1967 | McCormick | 425/117 |
| 3,411,185 | 11/1968 | Pickett | 249/83 |
| 3,456,300 | 7/1969 | Pickett | 425/117 |
| 3,674,396 | 7/1972 | McCormick | 425/117 |
| 3,940,219 | 2/1976 | Pickett et al. | 425/117 |
| 3,982,862 | 9/1976 | Pickett et al. | 249/83 |

Primary Examiner—Jay H. Woo
Assistant Examiner—M. McGurk
Attorney, Agent, or Firm—Fitch, Even, Tabin & Flannery

[57] ABSTRACT

A tissue specimen processing capsule is provided which includes a pair of interlocking frames each having a porous web spread across its central openings for holding specimen in a region defined between the webs. The porous webs permit access to the specimen by processing and impregnating liquids. After the tissue specimen is processed, it is removed from the capsule and placed in a mold depression, and the empty capsule is placed over the depression. Molten casting material is poured into the mold to fill the depression and to cover the porous material. The molten casting material solidifies to form a tissue block with the capsule serving as a clampable base for an outwardly extending, tissue-containing portion. The capsule may be formed in a single operation in an injection molding process using a press that includes a pair of mold blocks that together define frame-forming cavities and between which is sandwiched a segment of an elongated web of porous material. Molten plastic, injected into the cavities, forms the frames and impregnate portions of the web within the cavity, and the molten plastic solidifies with the porous material permanently affixed to newly molded frames.

6 Claims, 15 Drawing Figures

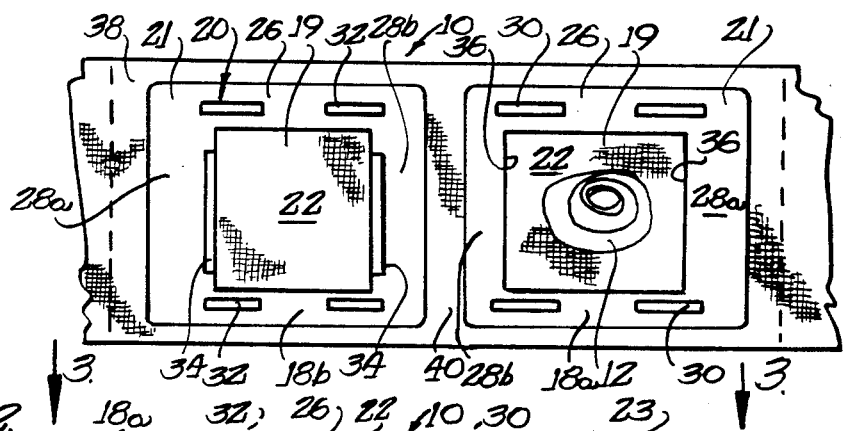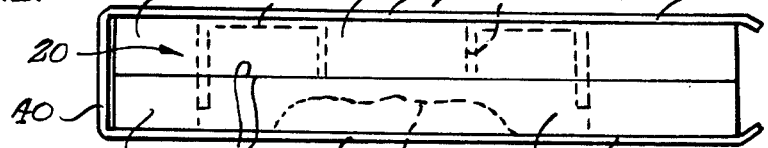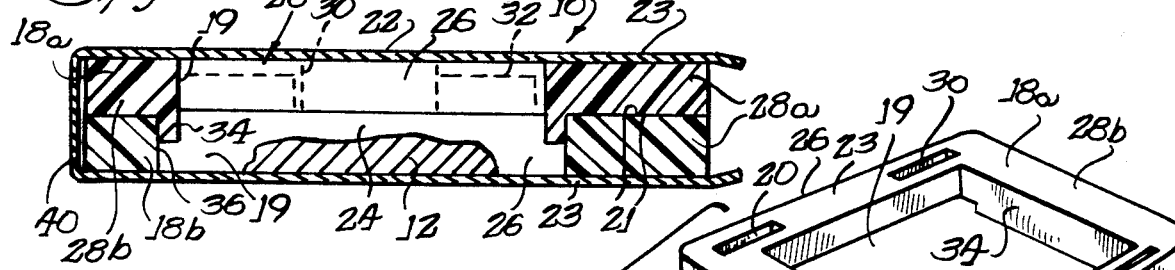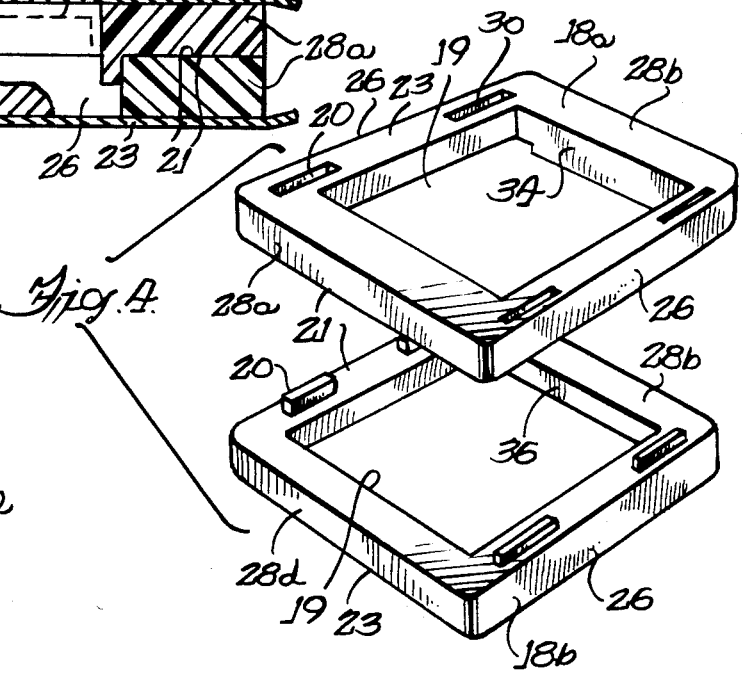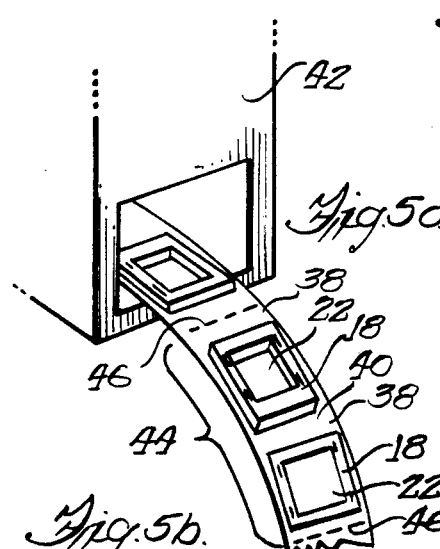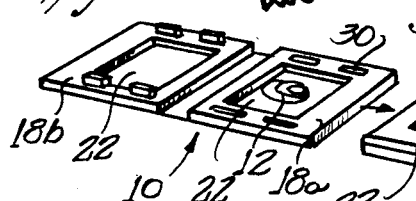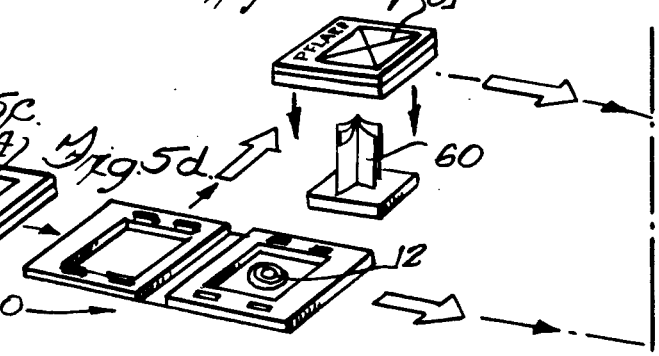

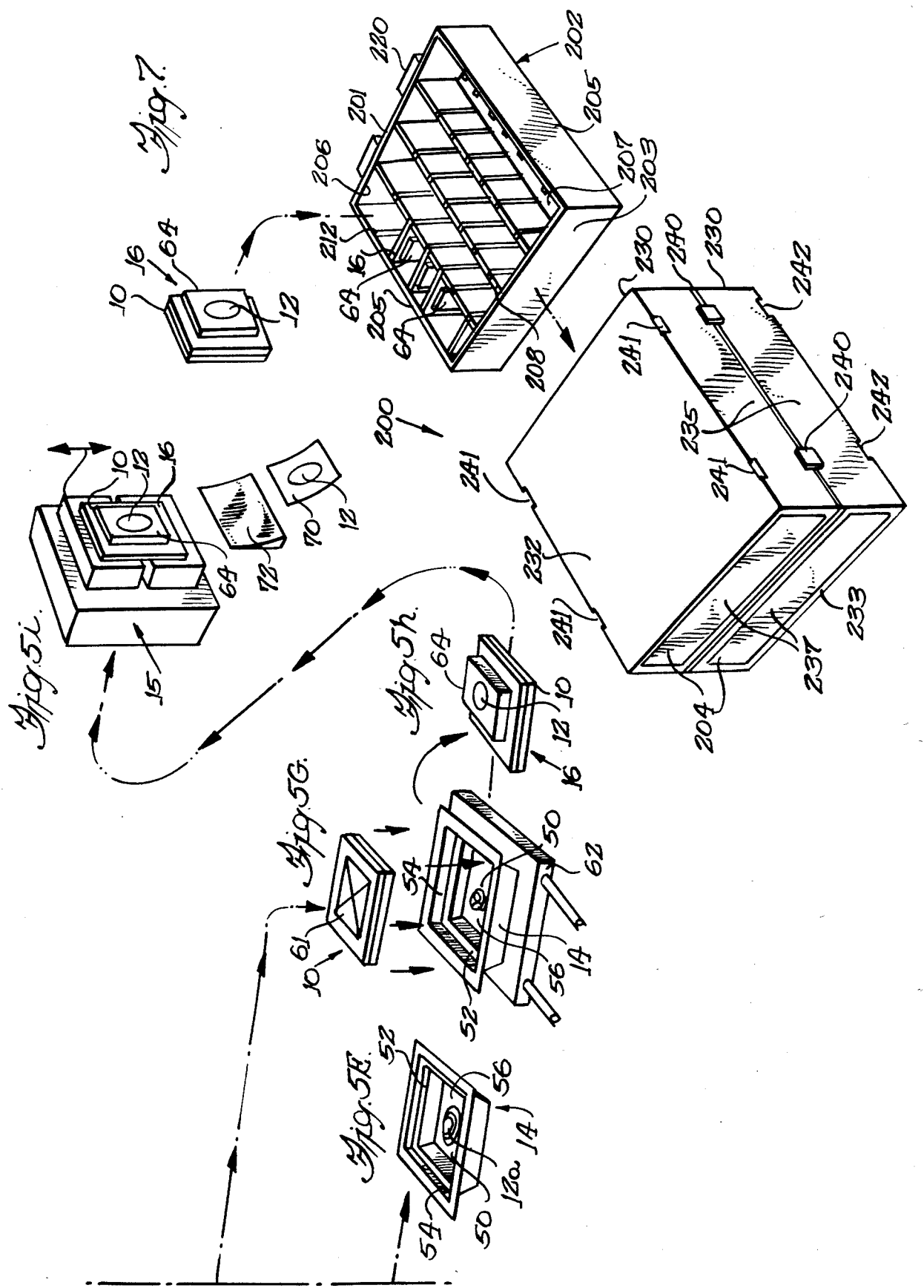

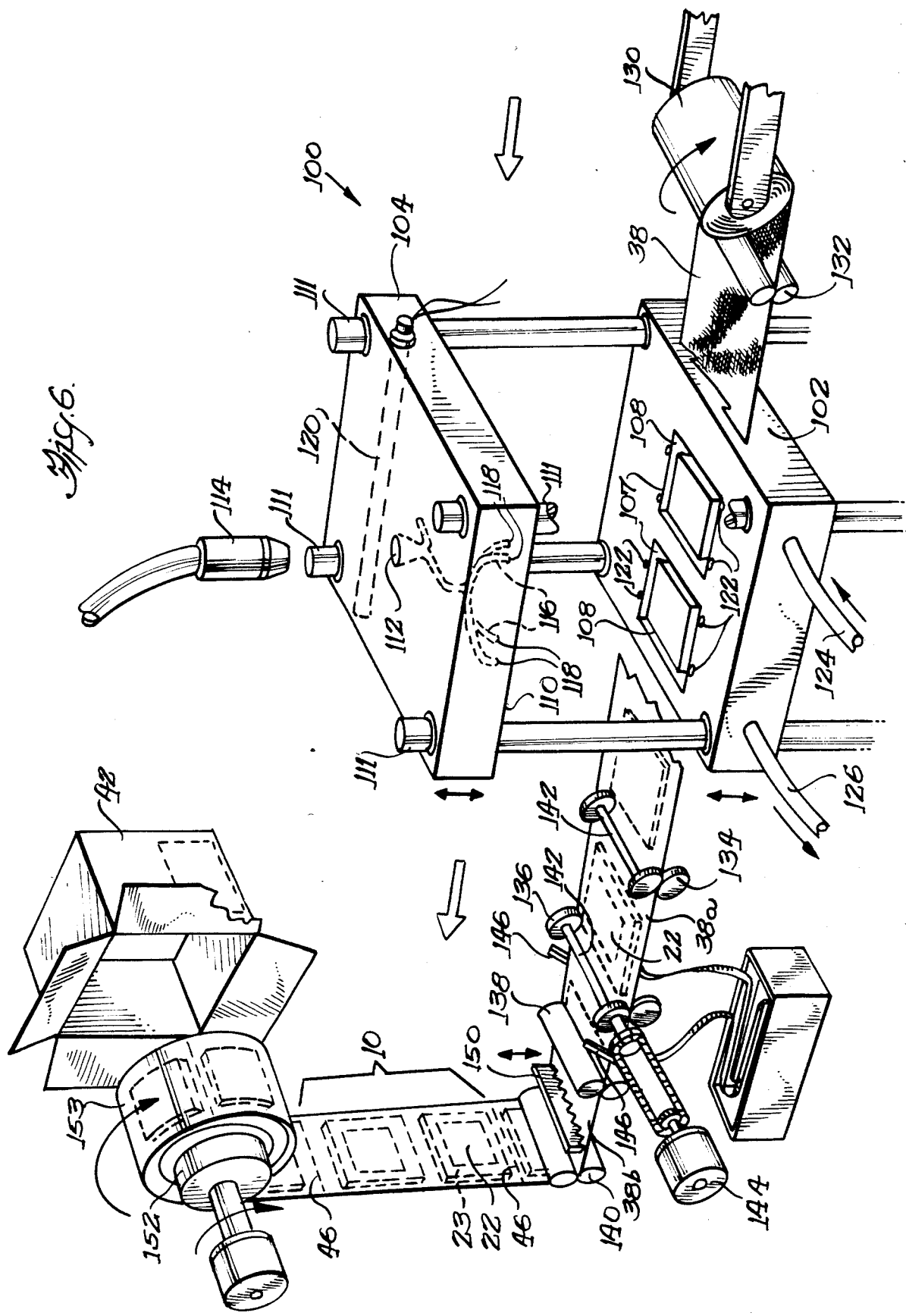

APPARATUS FOR PREPARING AND EMBEDDING TISSUE SAMPLES FOR HISTOLOGICAL EXAMINATION

The present invention relates to a capsule for preparing a tissue specimen for histological examination and to a method of manufacturing the capsule.

BACKGROUND OF THE INVENTION

It is a standard procedure to prepare tissue samples for microscopic examination by embedding the tissue in paraffin and slicing the paraffin-embedded tissue very thinly with a microtome. Preparatory to embedding, the tissue is treated in various solutions appropriate to its examination and long-term stability. Typically, prior to paraffin embedding, the tissue sample is fixed, dehydrated, cleared, infiltrated with molten paraffin and, depending on the test, stained.

A histology laboratory daily receives a large number of tissue samples for examination, and it is important that the tissues be prepared as efficiently as possible. Described in my U.S. Pat. No. 3,674,396 are capsules in which a tissue sample is prepared for embedding through exposure to various solutions within a capsule and then embedded. In these capsules, perforated walls are used to retain the tissue while accessing to the tissue the various solutions and, finally, molten paraffin. The perforations are of a minimal size; any substantial reduction in perforation size would reduce the efficiency of tissue processing and would be inappropriate for molding by current technology.

Typically, the tissue sample for examination is a unitary connected portion of tissue; however, small parts of the tissue sample may be dislocated during tissue processing. Alternatively, a biopsy may be performed on minute fragments less than about 0.1 mm. in diameter, such as bronchial washings, cytology preparations and aspiration biopsies which may be gathered by the new skinny needles. If several tissue capsules are processed together, the processing solutions may carry these tiny tissue particles or "floaters" from one sample to another. The transfer of even very minute particles of tissue from one sample to another may result in misleading diagnoses, particularly where the object of the examination is to detect invasion of the tissue by foreign cells, e.g., to determine whether a tumor has metastased.

It is a primary object of the present invention to provide improved capsules in which tissue specimens can be processed and embedded at maximum efficiency and without cross-contamination from one sample to another. It is a further object of the invention to manufacture such capsules inexpensively and to provide the capsules in a convenient form to the technician. It is a further object of the invention to provide a storage system for the prepared and embedded specimens.

SUMMARY OF THE INVENTION

The invention provides a capsule for processing and embedding tissue specimens. The capsule includes a pair of frames, each defining an interior opening. The frames have complementary inner frame faces, and interfitting means for snapping the frames together, establishing peripheral contact between the complementary faces. Spread across each frame opening outward of its interior face is a web of porous material, and when the frames are snapped together, a tissue-containing region is defined between the webs. The porous material webs access processing liquids and liquified embedding material to the tissue-containing region but prevent escape of tissue particles. Subsequent to processing and embedding, the tissue sample is transferred to a casting mold having a lower depression and an upper portion adapted to receive the emptied capsule. Additional liquified embedding material is poured into the mold, filling the depression and the interior region of the capsule, thereby casting a block which includes the capsule serving as the base of the block and an outwardly protruding, specimen-containing block portion that was formed in the depression. The base is insertable in a microtome chuck with the embedded specimen exposed to a microtome blade.

Capsules are inexpensively manufactured in a press having a pair of molding blocks that are reciprocal in and out of contact with each other and which, when brought together, define frame forming cavities. With the blocks spread apart, an elongated web of porous material is advanced between the blocks. After the blocks are brought together, sandwiching a segment of the web between the blocks, a molten thermoplastic is injected to fill the cavities, impregnating those portions of the web within the cavities. When the plastic solidifies to form the frames, the web is affixed by the plastic to the frame. The extended web, on which the frames are molded, can be coiled into a dispensing package from which a technician can cut or tear one pair of complementary frames at a time.

To aid in preserving the cast specimens, a drawer-cabinet arrangement is provided in which a broad top-loading drawer, having guides for receiving the capsule bases of the cast blocks, fits into an individual cabinet. The cabinets have notches along their top and bottom edges for receiving clip locks, whereby the individual cabinets can be locked together in a stack for long-term storage, occupying only the storage space actually required.

BRIEF DESCRIPTION OF THE DRAWINGS

FIG. 1 is a plan view of a tissue capsule laid out showing adjacent bottom and top frames, embodying various features of the present invention.

FIG. 2 is a side elevation view of a closed capsule of FIG. 1 with the top disposed over the bottom.

FIG. 3 is a cross-sectional view taken along line 3—3 of FIG. 2.

FIG. 4 is a perspective view of a pair of molded plastic frames shown in spaced relation without the associated webs of porous material.

FIGS. 5a–5i illustrate steps of a tissue preparation specimen process performed using the tissue capsule of FIG. 1 from tissue capsule dispensing to microtome slicing of a tissue specimen-containing cast block, FIGS. 5(e) and 5(g)–(i) being on a separate sheet.

FIG. 6 is a diagrammatic view of apparatus used for manufacturing the tissue capsules of FIG. 1.

FIG. 7 is a perspective view of a tissue-containing cast block storage system, embodying various features of the present invention.

DETAILED DESCRIPTION OF THE PREFERRED EMBODIMENTS

The invention provides a simple, inexpensively manufactured capsule 10 for holding a tissue specimen 12 as it is processed with various liquids and impregnated with a liquified embedding material. The capsule 10 subsequently fits over a mold 14 (FIG. 5e) to which the processed tissue specimen is removed, and liquified embedding material is poured into the mold to cast a tissue-containing block 16 (FIG. 5h) of which the capsule 10 serves as a base. The capsule base can then be placed in a microtome chuck 15 (FIG. 5i) so that the tissue-containing block 16 can be sliced.

The capsule 10 includes a pair of frames 18a, 18b, each having an inner face 21 and an outer face 23 and defining a large central opening 19. Each frame 18a and 18b has a web of porous material 22 spread across its opening 19 across its outer face 23, and the frames have means 20 for interlocking together to place their inner faces 21 in contact so that a tissue-holding interior region 24 (FIG. 3) is defined between the webs of porous material. The porous material 22 provides access to the interior region 24 to permit tissue processing liquids and liquified embedding material to enter the interior region 24 but retains the tissue specimen 12, including small particles (floaters) which may dissociate from the specimen.

Each frame 18a and 18b is molded as a unitary piece of thermoplastic material, such as a homopolymer acetal resin, sold under the trademark Delrin by Du Pont. The illustrated frames are rectangular, each including a pair of longer side segments 26 and a pair of shorter side segments 28. One of the shorter side segments 28a is wider than the opposite segment 28b, providing a labeling area. The inner and outer faces 21, 23 of each frame 18a and 18b are flat with the exception of the interlocking means 20.

Interlocking means 20 includes elongated slots 30 that extend entirely through the longer segments 26 of one frame 18a, and elongated tabs 32 that protrude from the inner face 21 of the other frame 18b to be snapped into a friction fit within the slots, holding the complementary inner faces in peripheral contact with each other. Secondary interfitting means comprise opposed tabs 34 which protrude from the interior face of the slotted frame 18a and which are extendable into the opening 19 of the other frame 18b to establish a friction fit with the interior edges 36 of the shorter side segments 28 of the other frame 18b.

The porous material 22 is affixed to the entire exterior face 23 of each of the frames 18, extending across the frame opening 19, and when the frames are interlocked with their inner faces 21 in peripheral contact with each other, the tissue-containing region 24 that is defined between the webs of porous material 22 is equal in thickness to the combined thicknesses of the frames. To provide good access to processing liquids and liquified embedding material, the porosity of the material is preferably between about 25 percent and about 75 percent. A preferred porous material is non-woven nylon, such as that sold under the trademark Cerex by Monsanto.

Using molding apparatus described in greater detail hereinafter with reference to FIG. 6, the frames 18 are molded onto an elongated web 38 of the porous material 22; thus, the webs of porous material affixed to the outer faces 23 of the interlocking frames 18a and 18b are continuous and include a connecting segment 40 between the frames at least equal to the combined thicknesses of the frames. This connecting segment 40 serves as a hinge and also serves to keep the frames connected when they are not interlocked. The frame pairs that are molded onto the continuous web 38 of porous material 22 are preferably dispensed from a package 42 (FIG. 5a) in which the continuous web is reeled. At the time of use, a portion 44 (FIG. 5a) of the continuous web, containing a paired set of frames 18a and 18b, is detached from the reel, as by cutting, but preferably by tearing along preformed perforation lines 46.

After being dispensed from the package 42, the paired frames 18a and 18b are placed porous material 22 side down (FIG. 5b) on a flat surface, and a tissue specimen 12 is placed on the porous material 22 of one frame 18a. Then the other frame 18b is closed over the one frame and the frames are snapped together, enclosing the specimen in the region 24 between the webs of porous material (FIG. 5c). Processing liquid, including fixatives and drying agents, are caused to flow through the porous material 22 and through the interior region 24 of the capsule 10. Finally, molten embedding material is introduced through the porous material 22 into the capsule, and the capsule is placed in a chamber (not shown) where it is subjected to vacuum, drawing the molten embedding material into the interstices of the tissue specimen 12. Excess embedding material is then drained from the capsule.

Because the specimen 12 is contained within a region 24 from which floaters cannot escape, even as the several liquids are caused to flow through the capsule 10, multiple capsuled specimens can be processed together. For example, a number of capsules 10 might be stacked together and liquids caused to flow through a central passageway defined by the aligned openings 19 of a stack of frames 18a and 18b.

Next, the capsule 10 is opened (FIG. 5d) and the wax impregnated tissue specimen 12a is removed from the capsule 10 to the mold 14 (FIG. 5e) for casting into the block 16. The mold 14 is configured generally as a rectangular pan, including a central depression 50 in which the wax-impregnated specimen 12a is placed, a horizontal peripheral ledge 52, and an upstanding lip 54 at the edges of the ledge that is adapted to receive the outer edges of the capsule 10 in a close fit. The wax-impregnated specimen 12a is positioned on the flat lower surface 56 of the depression which is preferably prewarmed so that when the specimen 12a is placed on the surface it becomes tacky. The technician precisely positions the tacky specimen 12a on the lower surface and then allows the mold 14 to cool, "freezing" the specimen into the selected position that is appropriate for subsequent slicing and examination.

The capsule 10, emptied of its contents, now is used for a secondary purpose, i.e., to provide a base for the cast block 16. The frames 18a and 18b of the emptied capsule are resnapped together, and the porous materials 22 are cut from corner to corner (FIG. 5f) with a crossed-blade knife 60 to provide an opening 61 for pouring embedding material. The empty capsule 10 is then placed (FIG. 5g) on the mold 14, resting on the horizontal ledge 52 and with its cut webs 22 aligned with the open upper end of the depression 50. Molten embedding material is poured through the cut webs, completely filling the depression and substantially filling the interior region 24 of the capsule 10 so that both cut webs of porous material 22 are submerged in the embedding material. The mold is placed on a cooling surface 62 (FIG. 5g), solidifying the embedding material and creating the cast block 16 (FIG. 5h) that includes the capsule 10 as its base and a protruding portion 64 having the tissue specimen 12 disposed adjacent its front surface 66.

As seen in FIG. 5i, the capsule 10, serving as the base of the block 16, is insertable within a microtome chuck 15, such as a spring-loaded chuck, and slices 70 are shaved from the block 16 with the blade 72 of the microtome. The remainder of the cast block 16 may be stored, so that if reexamination of tissue or confirmation of results is required, additional slices may be shaved.

In accordance with another aspect of the present invention, the tissue capsules 10 are formed in a one step injection molding process which forms the frames 18a and 18b described above, with the porous material 22 integrally affixed to the flat outer faces 23 of the frames. Illustrated in FIG. 6 is apparatus in which an elongated web 38 of porous material is drawn through a press 100 and sandwiched between molding blocks 102, 104 of the press, the web extending across block cavities 108 that are configured to mold the frames 18a and 18b. When a thermoplastic is injected into the cavities 108, the plastic impregnates portions of the porous material within the cavities, and the plastic solidifies with the porous material permanently affixed in the plastic of the frames 18a and 18b.

The press 100 is a conventional thermoplastic injection molding press and includes a lower block 102 into which are formed frame-shaped depressions 107 that help to define the enclosed cavities 108 and an upper block 104 having a flat lower surface 110 which covers the depressions 107 and through which molten plastic is introduced into the cavities. The blocks 102, 104 are each vertically reciprocal relative to each other. Pins 111 extend through the corners of the blocks for guiding the reciprocating blocks in precise alignment with each other.

The upper block 104 has an injection orifice 112 which receives a hot plastic injection nozzle 114, a channel or runner system 116 that carries molten plastic to point orifices 118 and a hot rod heater 120 that maintains a high temperature in the upper block 104, preventing plastic from solidifying within the channels 116. The lower block 102 includes the depressions 107 which are configured to form the interlocking slots 30 and tabs 32, 34. Injection points 122 are aligned with the point orifices 118 of the upper block 104 to receive the molten plastic from the channels 116. The lower block 102 also includes a cooling system, represented in FIG. 6 by a coolant inlet line 124 and a coolant outlet line 126.

Frames 18a, 18b are directly molded onto the continuous web 38 in an intermittent process. A series of sets of upper and lower rollers 132, 134, 136, 138, and 140 define a generally horizontal pathway for the continuous web which is intermittently drawn from a feed roll 130 to the press 100 and beyond. A roller set 132 upstream of the press 100 extends fully across the web 38; however, the roller sets 134, 136 immediately downstream of the press, consist of rollers that are disposed at the ends of connecting shafts 142, contacting the lateral edges of web 38 and straddling the newly molded frames 18. At least one set 136 of downstream rollers is powered by an intermittently operable motor 144 to advance newly molded frame pairs 18a and 18b from the region of the press 100, draw additional web 38 from the feed roll 130 and position fresh web within the region of the press.

With the web 38 stationary and a fresh segment of the web positioned between the press blocks 102, 104, the upper block 104 is reciprocated downward along the guide pins 111 and the lower block 102 is reciprocated upward along the guide pins 111 until they are brought together at the plane of the web pathway, tightly sandwiching the web therebetween. The nozzle 114 is lowered by a mechanism (not shown) into the injection orifice 112, and molten plastic is injected into the cavities 108. The cooling system of the lower block 102 speeds solidifying of the plastic within the cavities 108, and after sufficient time has passed to allow the plastic to solidify, the blocks 102, 104 are reciprocated apart, leaving the molded frames 108 affixed to the continuous web 38. The motor 144 is then operated to register the web 38 downstream, advancing the newly molded frame pair downsteam of the press and placing a fresh web section in the region of the press.

Downstream of the pulling roller set 136 is another roller set 138 that extends across the frame-carrying web 38a and which has a resilient gripping surface that allows the bulky frames 18a and 18b to pass therebetween. The resilient roller set 138 is linked, e.g., by a belt, to the motor-powered roller set 136 and advances the web 38a to a similar extent. Between the powered roller set 136 and the resilient roller set 138 is disposed a set of blades 146 positioned to trim excess web from the lateral sides of the frames.

Downstream of the resilient roller set 138 is an additional set of resilient rollers 140, which move the trimmed web 38b in registration with the intermittent passage of the web through the press 100. Intermediate the sets of resilient rollers 138, 140 is disposed a reciprocating knife 150 which provides a perforation line 46 between adjacent frame pairs while a pair of frames 18a and 18b are being molded in the press. The downstream resilient rollers 140 advance the web while applying a very light pulling force so as not to tear the web along the perforation lines 46.

Downstream of the roller sets is a spool 152 that takes up the frame-carrying web in registration with web played out from the feed reel 130. The take-up spool 152 is associated with packaging apparatus that winds web reels 153 containing a predetermined number of connected frame pairs for insertion into each dispensing package 42. Suitable packaging apparatus is known in the art and is not described in detail herein.

The invention further provides a drawer-cabinet, indicated generally at 200 in FIG. 7, for storing the cast blocks 16 for future reference. Slide drawers 202 have associated cabinets 204 that are stackable and lockable together, allowing space-consuming specimen drawer-cabinets to be added only to the extent needed and allowing individual specimen-filled drawer-cabinets to be removed to more remote storage areas on an individual basis after passage of time.

The drawer 202 is a low-slung, top loading rectangular box, including a front panel 201, a rear panel 203, opposed side panels 205, and a bottom 207, the drawer having an open top. A plurality of longitudinal dividers 208 run from the front to the rear of the drawer 202. The dividers 208 and side panels 205 are provided with guide channels 212 for receiving opposite edges of capsules 10 that are serving as bases of cast blocks 16. The guides channels 212 are spaced apart sufficiently to accommodate the protruding portions 64 of the blocks 16. The number of blocks stored in each drawer 202 and the number of capsules 10 reeled into each dispenser package 42 may be coordinated, and the capsules and drawer may be prelabeled with corresponding indicia. Handles 220 on the front panel 201 of each drawer 202 facilitate sliding the drawer in the cabinet 204.

The cabinet 204 comprises a low slung rectangular box, including a top panel 232, a bottom panel 233, opposed side panel 235, and a rear panel 237, leaving an open front end for receiving the drawer 202. Each of the opposed side panels 235 has one or more notches 241 closely adjacent to its upper edge and a corresponding number of vertically aligned notches 242 closely adjacent to its bottom edge. The notches are each adapted to receive a clip lock 240, and when cabinets are stacked together, clip locks 240 are inserted into the upper edge notches 241 of one cabinet and into the adjacent lower edge notches 242 of the cabinet stacked on top. In this manner, a plurality of clip-locked drawer-cabinets 200 form a unitary storage assembly.

A technician may keep a single drawer-cabinet 200 on his bench at all times, placing blocks 16 of embedded specimens in the drawer guides 212 in consecutive order. In between placing specimens in the drawer 202, the drawer is kept within the cabinet 204 to keep dust from the blocks 16. When the drawer 202 is filled, it is placed in its associated cabinet 204 and transported to a storage area where it is clip-locked to the top of a number of similarly stacked drawer-cabinets 200. The clip-locked cabinets form a secure, self-standing stack. As the stack only contains filled cabinets, no more storage area is occupied than is required. When an immediate storage area is fully occupied, a portion of the stack containing earlier filled-cabinets may be separated, and the earlier-filled portion of the stack removed to a more remote storage area.

Several advantages of the invention can now be more fully appreciated. The capsule 10 provides excellent exposure of a tissue specimen 12 to processing liquids and embedding material and at the same time securely retains all portions of the specimen, including floaters, so that multiple tissue specimens can be processed together with no danger of cross-contamination. The capsule 10 provides several features which facilitate its use by a technician, including its simple interlocking mechanism, its dispensibility from a package and the interconnecting web, that in addition to defining the tissue-containing region, includes a hinge segment that keeps the paired frames together. The capsule is self-conserving, performing a dual role, first as a processing capsule, and secondly, through its use in conjunction with a casting mold 14, as a clampable base of a cast block 16.

Very importantly, the capsules are manufactured by a one step molding process which forms the frames 18a and 18b and at the same time affixes the frames to the porous material 22. This method of manufacture allows the capsules 10 to be formed very inexpensively.

While the invention has been described in terms of certain preferred embodiments, modifications obvious to one with ordinary skill in he art may be made without departing from the scope of the invention. For example, with a different arrangement of interlocking tabs and slots, both frames which form a capsule could be identical, in which case a mold press could be used having a single frame cavity.

Various features of the invention are set forth in the following claims.

What is claimed is:

1. A capsule for receiving and retaining a tissue specimen during fluid treatment preparatory to histological examination comprising a pair of frames, each of said frames defining a central opening, said frames having complementary faces adapted to abut one another in face-to-face registered relationship, the openings within said abutting frames defining a fluid passageway for tissue treating fluids, a porous web spanning the central opening of each of said frames, said webs being spaced apart when said frames are in abutting relationship defining therebetween a tissue receiving cavity, said web having a porosity that retains all portions of a tissue specimen placed in said cavity while permitting fluid flow therethrough, said web being easily cuttable to permit submerging of said web in embedding medium when said capsule is used as the base for an embedded tissue block, and means for maintaining said frames in abutting relationship.

2. A capsule in accordance with claim 1 wherein said frames are molded to said web.

3. A capsule in accordance with claim 2 wherein said web has a porosity of between about 25 and about 75 percent.

4. A capsule for receiving and retaining a tissue specimen during fluid treatment preparatory to histological examination comprising a web of porous facric, a pair of complementary frames affixed to said web in spaced aligned relationship, each of said frames defining a central opening spanned by said web, said frames having complementary faces adapted to abut one another in face-to-face registered relationship, the portions of said web spanning said frames being spaced apart when said frames are in abutting relationship defining therebetween a tissue receiving cavity, said frames being spaced apart a distance such that the portion of said web between said frames functions as a hinge when said faces are abutted, and means for maintaining said frames in abutting relationship.

5. A capsule in accordance with claim 4 wherein said frames are molded to said web.

6. A capsule in accordance with claim 4 wherein said web has a porosity of between 25 and 75 percent.

* * * * *

UNITED STATES PATENT AND TRADEMARK OFFICE
CERTIFICATE OF CORRECTION

PATENT NO. : 4,557,903

DATED : December 10, 1985

INVENTOR(S) : James B. McCormick

It is certified that error appears in the above-identified patent and that said Letters Patent is hereby corrected as shown below:

Column 7, Line 53, change "he" to --the--.

Column 8, Line 36, change "facric" to --fabric--.

Signed and Sealed this

First Day of April 1986

[SEAL]

Attest:

DONALD J. QUIGG

Attesting Officer

Commissioner of Patents and Trademarks